(12) United States Patent
Chen (10) Patent No.: US 12,194,313 B2
(45) Date of Patent: Jan. 14, 2025

(54) RADIATION TREATMENT SYSTEM AND OPERATION PROCEDURE OF IRRADIATION PARAMETER VERIFICATION DEVICE

(71) Applicant: NEUBORON THERAPY SYSTEM LTD., Fujian (CN)

(72) Inventor: Wei-Lin Chen, Fujian (CN)

(73) Assignee: NEUBORON THERAPY SYSTEM LTD., Xiamen (CN)

( * ) Notice: Subject to any disclaimer, the term of this patent is extended or adjusted under 35 U.S.C. 154(b) by 246 days.

(21) Appl. No.: 18/075,547

(22) Filed: Dec. 6, 2022

(65) Prior Publication Data

US 2023/0097916 A1 Mar. 30, 2023

Related U.S. Application Data

(63) Continuation of application No. PCT/CN2021/088672, filed on Apr. 21, 2021.

(30) Foreign Application Priority Data

Jun. 8, 2020 (CN) .......................... 202010510248.8

(51) Int. Cl.
*A61N 5/10* (2006.01)
*A61N 5/00* (2006.01)

(52) U.S. Cl.
CPC ......... *A61N 5/1049* (2013.01); *A61N 5/1045* (2013.01); *A61N 5/1071* (2013.01);
(Continued)

(58) Field of Classification Search
CPC .. A61N 5/1045; A61N 5/1049; A61N 5/1071; A61N 2005/1061;
(Continued)

(56) References Cited

U.S. PATENT DOCUMENTS 9,498,167 B2 * 11/2016 Mostafavi ................ A61N 5/10

FOREIGN PATENT DOCUMENTS

| CN | 107297031 A | 10/2017 |
| CN | 109011221 A | 12/2018 |

(Continued)

OTHER PUBLICATIONS

International Search Report of PCT/CN2021/088672, Jul. 21, 2021.

*Primary Examiner* — Mark R Gaworecki
(74) *Attorney, Agent, or Firm* — Locke Lord LLP; Tim Tingkang Xia, Esq.

(57) ABSTRACT

A radiation treatment system and an operation procedure of an irradiation parameter verification device. The radiation treatment system comprises a radiation generation device, an irradiation chamber used for placing a patient, a carrying device used for transferring and bearing the patient, a collimator provided in the irradiation chamber, an irradiation parameter verification device used for determining whether the position of the patient is suitable for performing radiation irradiation treatment or not, and a collimator model, wherein the collimator comprises a collimator outlet; the collimator model comprises a collimator model outlet; the shape and the size of the collimator model outlet are the same as those of the collimator outlet, and the size of the collimator model in the direction perpendicular to the collimator model outlet is smaller than the size of the collimator in the direction perpendicular to the collimator outlet.

20 Claims, 4 Drawing Sheets

(52) U.S. Cl.
CPC .............. *A61N 2005/1061* (2013.01); *A61N 2005/1063* (2013.01); *A61N 2005/1072* (2013.01); *A61N 2005/109* (2013.01)

(58) Field of Classification Search
CPC .... A61N 2005/1063; A61N 2005/1072; A61N 2005/109
See application file for complete search history.

(56) References Cited

FOREIGN PATENT DOCUMENTS

| | | | |
|---|---|---|---|
| CN | 109925612 | A | 6/2019 |
| CN | 110664429 | A | 1/2020 |
| CN | 212880642 | U | 4/2021 |
| JP | 2002306617 | A | 10/2002 |
| JP | 2014161623 | A | 9/2014 |
| JP | 2016077812 | A | 5/2016 |
| WO | 2019116678 | A1 | 6/2019 |
| WO | 2019119835 | A1 | 6/2019 |

* cited by examiner

RADIATION TREATMENT SYSTEM AND OPERATION PROCEDURE OF IRRADIATION PARAMETER VERIFICATION DEVICE

CROSS-REFERENCE TO RELATED PATENT APPLICATION

This application is a continuation application of International Application No. PCT/CN2021/088672, filed on Apr. 21, 2021, which claims priority to Chinese Patent Application No. 202010510248.8, filed on Jun. 8, 2020, the disclosures of which are hereby incorporated by reference.

TECHNICAL FIELD

The invention relates to a radioactive ray irradiation system, and in particular to a radiation ray therapy system and an operation procedure of an irradiation parameter verification device.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the disclosure.

With the development of atomics, radio therapy, such as cobalt sixty, a linear accelerator, an electron beam, or the like, has become one of the major means to treat cancers. During radiotherapy, it is required to use a beam to continuously irradiate a patient within a certain period of time. Before irradiation, it is required to position the patient to a suitable position, to ensure that radiation rays may kill tumor cells in the patient's body to a maximum extent and reduce damage caused by the radiation rays to normal tissues around the tumor cells as much as possible. The patient's position refers to position parameters of the patient's tumor center with respect to a center of a collimator, i.e., irradiation parameters. Each set of the irradiation parameters includes an irradiation point and an irradiation angle. After the irradiation parameters are known, it is verified whether dose distribution corresponding to a set of irradiation parameters meets requirements.

At present, an image acquisition device such as a computed tomography (CT) scanner or the like, is used to acquire image data of the collimator and the patient, and then irradiation parameters corresponding to the patient when the patient is located in the position are obtained by calculation. However, due to limitation of sizes of the collimator and the image acquisition device, the collimator with an excessive size cannot be transported together with the patient into the image acquisition device for radiography.

SUMMARY

In order to solve the above problems, the invention provides a radiation ray therapy system and an operation procedure of an irradiation parameter verification device, which do not have additional requirements for a size of a working range of the image acquisition device.

The radiation ray therapy system includes a radiation ray generation device, an irradiation chamber, a carrying device, a collimator, a collimator model, and an irradiation parameter verification device. The radiation ray generation device is configured to generate radiation rays for therapy. The irradiation chamber is configured to place the patient subjected to irradiation of the radiation rays therein. The carrying device is configured to transport and bear the patient. The collimator is arranged in the irradiation chamber and includes a collimator outlet through which the radiation rays emit. The collimator model includes a collimator model outlet with shape and size identical to shape and size of the collimator outlet respectively, a size of the collimator model in a direction perpendicular to the collimator model outlet is smaller than a size of the collimator in a direction perpendicular to the collimator outlet. The irradiation parameter verification device includes an image acquisition unit configured to acquire image data of the patient and the collimator model.

Further, the irradiation parameter verification device may further include a storage unit, a conversion unit, a calculation unit, and a comparison unit. The storage unit is configured to store the image data of the patient and the collimator obtained from the image acquisition unit. The conversion unit is configured to convert the image data of the patient and the collimator in the storage unit into irradiation parameters. The calculation unit is configured to calculate dose distribution of the radiation rays in the patient's body at a corresponding position, in combination with the irradiation parameters in the conversion unit. The comparison unit is configured to compare the dose distribution calculated by the calculation unit with a preset dose distribution.

Preferably, the image acquisition unit may include a CT scanner.

Further, the size of the collimator model in the direction perpendicular to the collimator model outlet may be 1 to 10 mm.

Further, one collimator model may have multiple collimator model outlets with different sizes, and shape and size of each of the collimator model outlets correspond to shape and size of a collimator outlet of a corresponding collimator respectively.

Preferably, multiple cavities with different sizes may be processed inside the collimator model, and each of the cavities with different sizes represents a corresponding collimator model outlet.

Preferably, multiple grooves with different sizes are formed at intervals on an end face where the collimator model outlet is located, and each of the grooves with different sizes represents a corresponding collimator model outlet.

Further, the radiation ray therapy system may further include an adjustment mechanism configured to adjust and fix a relative position between the patient and the collimator model.

The radiation ray therapy system may be a neutron capture therapy system.

Preferably, the neutron capture therapy system may be a boron neutron capture therapy (BNCT) system.

Further, the BNCT system is an accelerator BNCT system.

The operation procedure of the irradiation parameter verification device includes the following operations S1-S6. In operation S1, the carrying device moves to a working area of the image acquisition unit to acquire the image data of the patient and the collimator model. In operation S2, the storage unit stores the image data of the patient and the collimator model obtained from the image acquisition unit. In operation S3, the conversion unit converts the image data of the patient and the collimator model in the storage unit into the irradiation parameters. In operation S4, the calculation unit calculates dose distribution of the radiation rays in the patient's body when the patient is located at a position corresponding to the irradiation parameters, based on other information, such as beam intensity, tumor size, or the like, in combination with the irradiation parameters. In operation S5, the comparison unit compares the dose distribution calculated by the calculation unit with the preset dose distribution. In operation S6, a relative position between the collimator model and the patient is adjusted, and operations S1-S5 are repeated, until a difference between the dose distribution obtained from the calculation unit with the preset dose distribution is within an acceptable range.

Compared with the related art, technical solutions described in embodiments have the following advantageous effects. A collimator model including a collimator model outlet with shape and size identical to shape and size of the collimator outlet respectively but with a length smaller than a length of the collimator is transported together with the patient into the image acquisition unit, to acquire images thereof, so as to judge whether the patient's position relative to the collimator model outlet is suitable to perform irradiation therapy by radiation rays, it is unnecessary to place a complete collimator into the image acquisition unit, so that requirements for a size of a working range of the image acquisition unit are reduced, and manufacturing cost is reduced.

DETAILED DESCRIPTION OF THE DISCLOSURE

Embodiments of the invention will be further described in detail below with reference to the drawings, to enable those skilled in the art to implement the embodiments with reference to texts of the description.

In order to make objectives, technical solutions and advantages of the invention more apparent and clearer, the invention will be further described in detail below with reference to the drawings and the embodiments. Words "connect", "mount", "fix", or the like described in the following descriptions may indicate direct connection, mounting and fixation, or indicate indirect connection, mounting and fixation to allow to interpose third-party substance, or indicate detachable connection, mounting and fixation, or indicate non-detachable connection, mounting and fixation, unless indicated specifically.

Figure 1:
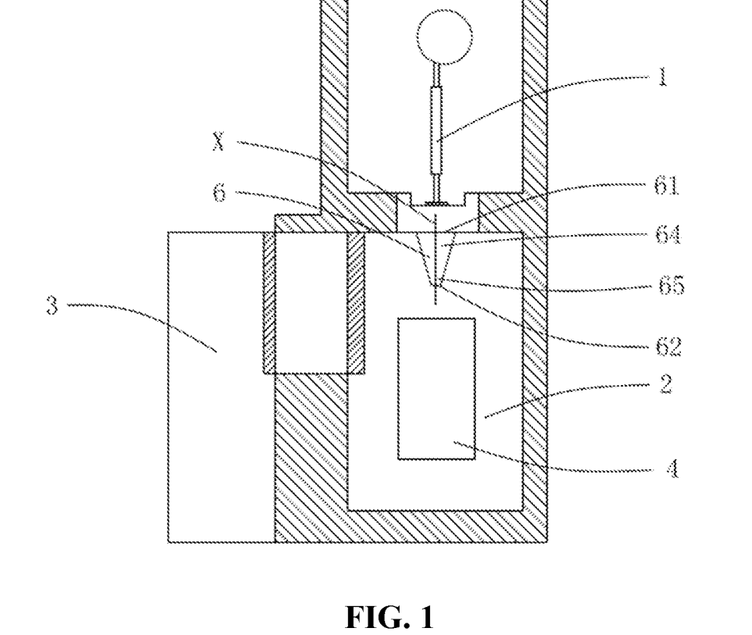
FIG. 1 is a top view of a radiation ray therapy system without an irradiation parameter verification device according to the invention.
Figure 2:
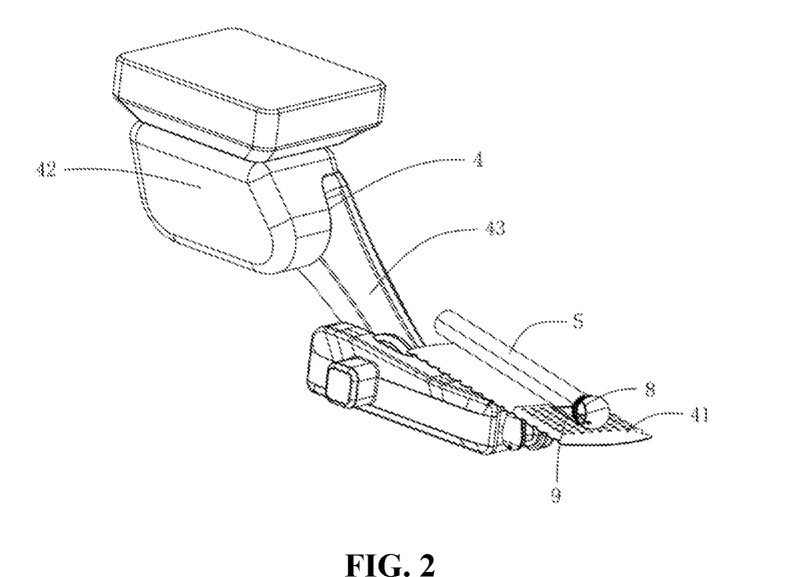
FIG. 2 is a schematic perspective view of a carrying device carrying a patient, an adjustment mechanism and a collimator model of a radiation ray therapy system according to the invention.
Figure 3:
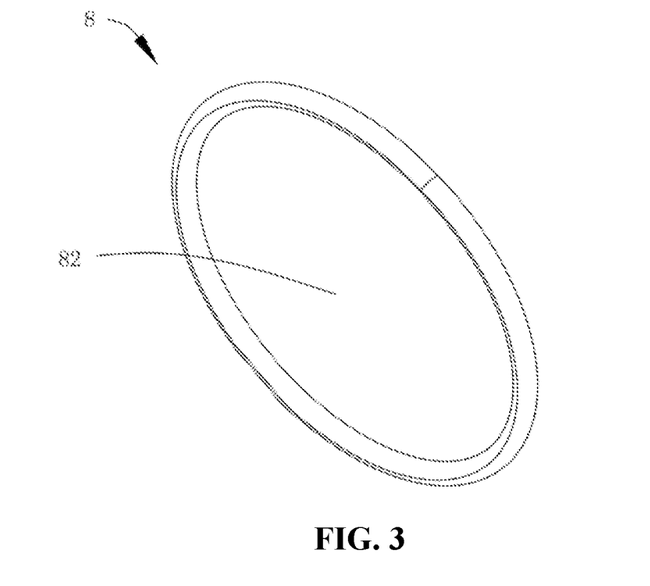
FIG. 3 is a schematic perspective view of a collimator model in a first embodiment of a radiation ray therapy system according to the invention.

Radiation ray therapy is a common means for treating cancers. As shown in FIG. 1 to FIG. 3, a radiation ray therapy system for performing radiation ray therapy includes a radiation ray generation device 1, an irradiation chamber 2, a management chamber 3, a carrying device 4, and an irradiation parameter verification device 5. The radiation ray generation device 1 is configured to generate radiation rays for therapy. The irradiation chamber 2 is configured to place a patient S subjected to irradiation of the radiation rays therein. The management chamber 3 is configured to implement irradiation control. The carrying device 4 is configured to transport and bear the patient S. The irradiation parameter verification device 5 is configured to determine whether the patient S is properly positioned.

Referring to FIG. 1, the radiation ray generation device 1 is configured to generate the radiation rays outside the irradiation chamber 2 and may irradiate the radiation rays to the patient S placed in the irradiation chamber 2. A collimator 6 is arranged in the irradiation chamber 2, and includes an inlet 61 through which the radiation rays enter and a collimator outlet 62 through which the radiation rays emit, a center line X of the collimator outlet 62 is aligned with a to-be-irradiated part of the patient S. The collimator 6 is divided into two parts, that is, a section of the collimator close to the inlet 61 is defined as a front end portion 64, a section collimator close to the collimator outlet 62 is defined as a rear end portion 65, and the rear end portion 65 of the collimator 6 has a size of 1 mm to 10 mm in a direction parallel to the center line X of the collimator 6. The management chamber 3 is a room for managing and controlling an overall therapy procedure of irradiating the radiation rays, for example, a manager confirms whether the patient S is positioned in place or not by his/her naked eyes from interior of the management chamber 3. The carrying device 4 is configured to carry the patient S to perform rotation, translation and lifting movement.

Referring to FIG. 2, the carrying device 4 includes a carrying member 41, a driving member 42, and a connection member 43. The carrying member 41 is configured to carry the patient S. The driving member 42 is configured to drive the carrying member 41 to rotate and/or move. The connection member 43 is connected between the carrying member 41 and the driving member 42. In the embodiment disclosed in the invention, the carrying member 41 is a flat bed plate, the connection member 43 is a mechanical arm, and the driving member 42 is a common power source or manual driver, such as a cylinder driving the mechanical arm to move, or the like. In other embodiments, the carrying member 41 may be configured as a carrying chair with a chair shape, and the connection member 43 may be configured as a linkage mechanism, of course, they are not limited to structures as listed above.

Before irradiation therapy is performed by the radiation rays, the manager needs to determine whether the patient S is positioned to a proper position, specifically, whether the patient S's position relative to the collimator outlet 62 is suitable to perform irradiation therapy by the radiation rays. When irradiation therapy is performed by the radiation rays based on a suitable position, the radiation rays may kill tumor cells in the patient S's body to a maximum extent and reduce damage caused by the radiation rays to normal tissues around the tumor cells as much as possible. Therefore, before irradiation therapy is performed by the radiation rays, the irradiation parameter verification device 5 is required to verify the patient S's position, to ensure that the patient S is located at a suitable to-be-irradiated position. The patient S's position refers to position parameters of the patient S's tumor center with respect to a coordinate origin, i.e., irradiation parameters. Each set of the irradiation parameters includes an irradiation point and an irradiation angle. In the embodiment disclosed in the invention, the irradiation parameters (X, Y, Z, (D) are determined by taking a center point of the collimator outlet 62 as the origin.

Referring to FIG. 3, the irradiation parameter verification device 5 includes an image acquisition unit 51, a storage unit 52, a conversion unit 53, a calculation unit 54, and a comparison unit 55. The image acquisition unit 51 is configured to acquire image data of the patient S and the collimator 6. The storage unit 52 is configured to store the image data of the patient S and the collimator 6 obtained from the image acquisition unit 51. The conversion unit 53 is configured to convert the image data of the patient S and the collimator 6 in the storage unit 52 into corresponding irradiation parameters. The calculation unit 54 is configured to calculate dose distribution of the radiation rays in the patient S's body at a position, in combination with the irradiation parameters in the conversion unit 53. The comparison unit 55 is configured to compare the dose distribution calculated by the calculation unit 54 with a preset dose distribution. The preset dose distribution is stored in the storage unit 52.

Figure 4:
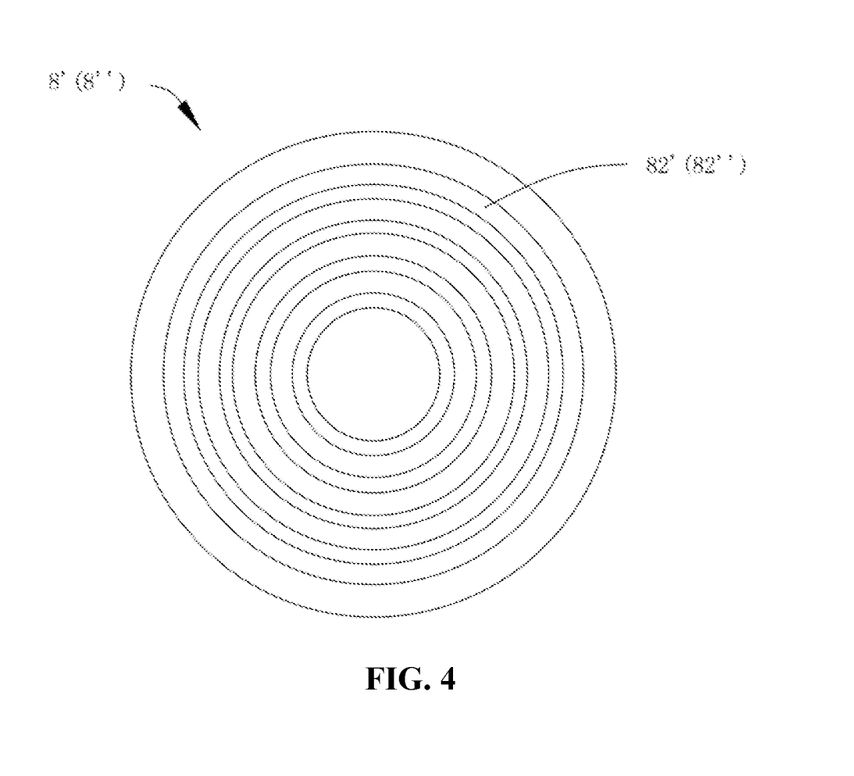
FIG. 4 is a front view of collimator models in second and third embodiments of a radiation ray therapy system according to the invention.

Referring to FIG. 1 and FIG. 4, a shape of the collimator 6 may be cylindrical, cuboid, conical, or the like, according to actual requirements. In the invention, a conical collimator 6 is used as an example, the collimator 6 has a length of 0 to 50 cm, the inlet 61 has a diameter of 0.5 to 30 cm, and an inlet of the image acquisition unit 51 has a size smaller than 100 cm. In a process of acquiring the image data of the patient S and the collimator 6, when the collimator 6 has a large size, the whole collimator 6 cannot be transported together with the patient S to interior of the image acquisition unit 51, to acquire images thereof. In an actual operation process, the conversion unit 53 only requires image data of a relative position between the collimator outlet 62 and the patient S, to obtain position parameters of the patient S's tumor center with respect to the coordinate origin (the center point of the collimator outlet 62), i.e., irradiation parameters. Specifically, only shape and size of the collimator outlet 62 and image data of a relative position between an end face of the collimator outlet 62 and the patient S are provided to the conversion unit 53, so that only a collimator model 8 capable of practically presenting the shape and size of the collimator outlet 62 is manufactured, and is transported together with the patient S to the interior of the image acquisition unit 51 for radiography. The collimator model 8 includes a collimator model inlet 81 and a collimator model outlet 82, a direction perpendicular to the collimator outlet 62 and the collimator model outlet 82 is defined as a length direction, and then the collimator model outlet 82 has shape and size identical to the shape and size of the collimator outlet 62 respectively, but the collimator model 8 has a length smaller than the length of the collimator 6.

In the invention, the collimator model 8 having shape and size completely identical to shape and size of the rear end portion 65 of the collimator 6 respectively is manufactured, and is transported together with the patient S to the interior of the image acquisition unit 51 for radiography. That is, in a direction parallel to the center line X of the collimator model 8, the collimator model 8 has a size of 1 mm to 10 mm.

In other embodiments, a simulated collimator with shape and size completely identical to shape and size of the collimator 6 respectively may be manufactured, the simulated collimator has definitions consistent with the inlet 61, the collimator outlet 62, the front end portion 64 and the rear end portion 65 of the collimator 6, and then the rear end portion 65 of the simulated collimator is taken as the collimator model 8, to be placed together with the patient S into a working range of the image acquisition unit 51 for radiography. Specifically, in a direction parallel to the center line X of the simulated collimator, the rear end portion 65 has a size of 1 mm to 10 mm.

In other embodiments, a hollow cylinder with shape and size identical to shape and size of the collimator outlet 62 respectively may be manufactured as the collimator model 8, to be placed together with the patient S into the working range of the image acquisition unit 51 for radiography, and in a direction parallel to the centerline X of the collimator model 8, the collimator model 8 has a size of 1 mm to 10 mm.

Figure 5:
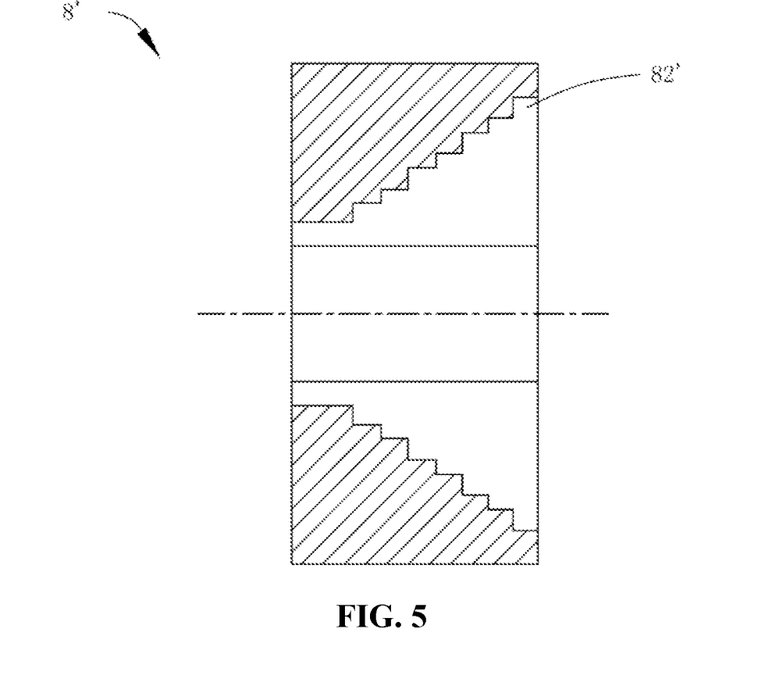
FIG. 5 is a cross-section view of a collimator model in a second embodiment of a radiation ray therapy system according to the invention.

Referring to FIG. 4 and FIG. 5, in order to adjust and fix a relative position between the patient S and the collimator model 8, the radiation ray therapy system further includes an adjustment mechanism 9 configured to adjust and fix the relative position between the patient S and the collimator model 8. Before the patient S and the collimator model 8 are transported into the working range of the image acquisition unit 51 for radiography, a doctor or physicist adjusts and fixes the collimator model 8 to a suitable position through the adjustment mechanism 9 according to his/her experience, and in this position, the patient S's tumor center corresponds to a set of irradiation parameters. Structure of the adjustment mechanism 9 is not limited, as long as the relative position between the collimator model 8 and the patient S may be adjusted and fixed.

Before performing irradiation therapy by the radiation rays, it is required to determine, by the irradiation parameter verification device 5, whether the patient S's position relative to the collimator model outlet 82 is suitable to perform irradiation therapy by radiation rays. Before verification, the doctor or physicist places and fixes the patient S at a corresponding position on the carrying member 41 according to his/her experience, and then adjusts a position of the collimator model 8 relative to the patient S and locks the collimator model 8. Specific operations are as follows.

In operation S1, the carrying member 41 moves to a working area of the image acquisition unit 51 to acquire the image data of the patient S and the collimator model 8.

In operation S2, the storage unit 52 stores the image data of the patient S and the collimator model 8 obtained from the image acquisition unit 51.

In operation S3, the conversion unit 53 converts the image data of the patient S and the collimator model 8 in the storage unit 52 into irradiation parameters corresponding to the position.

In operation S4, the calculation unit 54 calculates dose distribution of the radiation rays in the patient S's body when the patient S is located at a position corresponding to the irradiation parameters, based on other information, such as beam intensity, tumor size, or the like, in combination with the irradiation parameters.

In operation S5, the comparison unit 55 compares the dose distribution calculated by the calculation unit 54 with the preset dose distribution.

In operation S6, a relative position between the collimator model and the patient is adjusted, and operations S1-S5 are repeated, until a difference between the dose distribution obtained from the calculation unit 54 with the preset dose distribution is within an acceptable range.

After obtaining irradiation parameters to which a corresponding dose distribution is within the acceptable range, the driving member 42 of the carrying device 4 drives the carrying member 41 to move to the position corresponding to the irradiation parameters, to irradiate the radiation rays.

In the embodiment disclosed in the invention, the image acquisition unit 51 is a CT scanner, and in other embodiments, other devices may be selected to acquire images.

Figure 6:
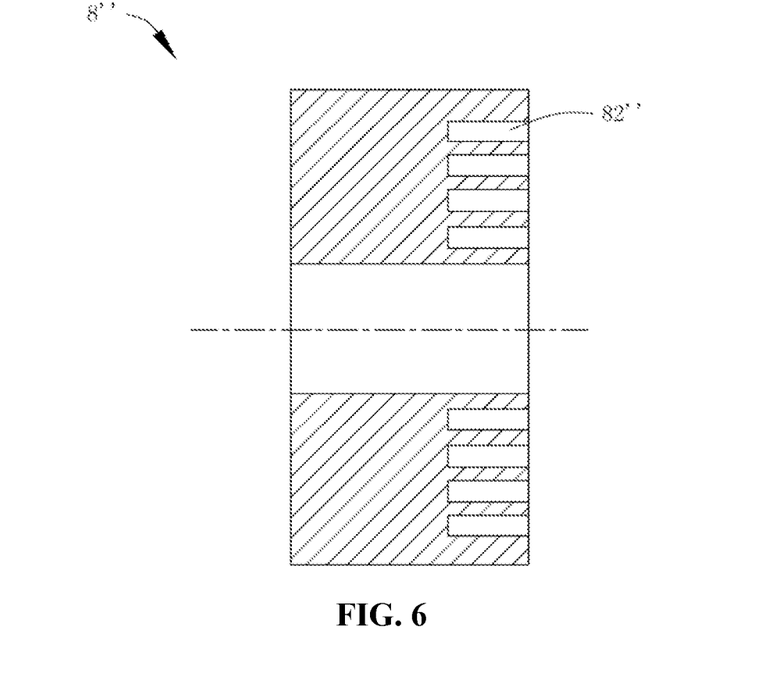
FIG. 6 is a cross-section view of a collimator model in a third embodiment of a radiation ray therapy system according to the invention.
Figure 7:
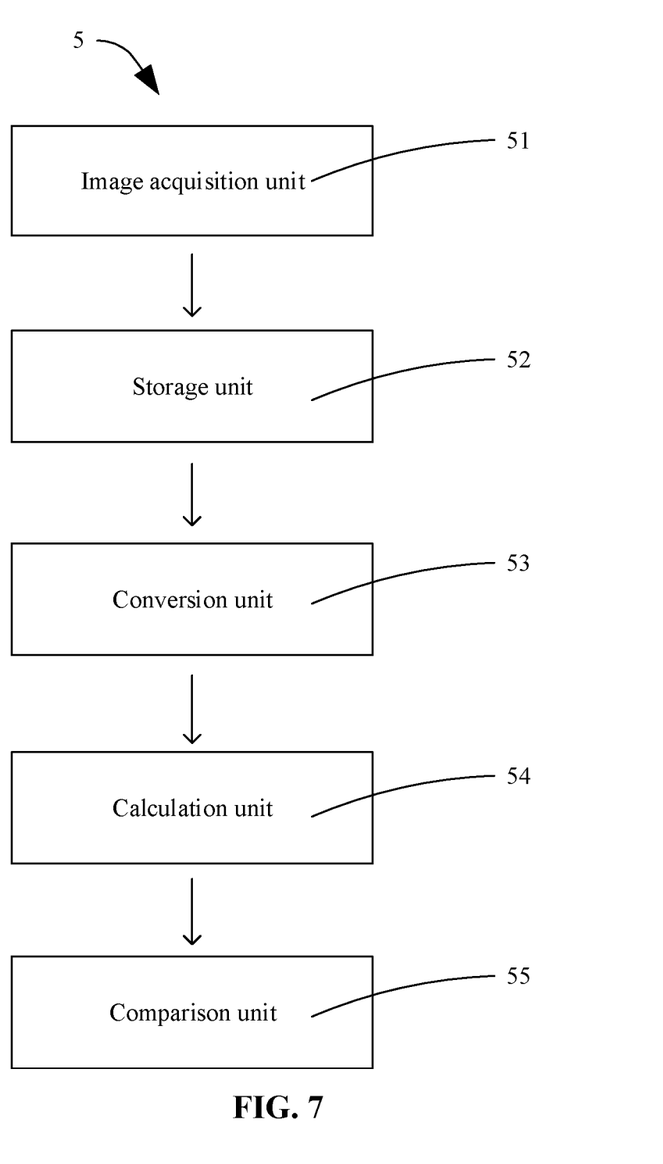
FIG. 7 is a schematic view of an irradiation parameter verification device of a radiation ray therapy system according to the invention.

In a first embodiment, an inner cavity of the collimator model 8 has a cylindrical shape, and one collimator model 8 corresponds to one collimator model outlet 82 with a unique shape and size, and in second and third embodiments, multiple collimator model outlets 82 with different sizes are marked on one collimator model 8', 8", to achieve a purpose of obtaining multiple sets of irradiation parameters by radiography once. Specifically, referring to FIG. 5, in the second embodiment, multiple cylindrical cavities 82' with different diameters are processed inside the collimator model 8', in a direction parallel to a center of the collimator model 8', and referring to FIG. 6, in the third embodiment, multiple annular grooves 82" with different diameters are formed at intervals on an end face of the collimator model 8", here center lines of the multiple cylindrical cavities 82' coincide, and center lines of the multiple annular grooves 82" coincide. Each cylindrical cavity 82' and annular groove 82" with different diameters represent a corresponding collimator model outlet 82. The cylindrical cavity 82' and the annular groove 82" correspond to a circular collimator outlet 62, and when the collimator outlet 62 has a square shape or another shape, the cylindrical cavity 82' and the annular groove 82" are correspondingly replaced by a square cavity, a square groove, or the like. Preferably, in a direction from the collimator model outlet 82 to the collimator model inlet 81, a diameter of the cylindrical cavity 82' processed inside the collimator model 8' gradually decreases.

According to the invention, a collimator model 8 including a collimator model outlet 82 with shape and size identical to shape and size of the collimator outlet 62 respectively but with a length smaller than a length of the collimator 6 is used, and is transported together with the patient S into the interior of the image acquisition unit 51 for radiography, it is unnecessary to place a complete collimator 6 into the image acquisition unit 51, so that requirements for a size of a working range of the image acquisition unit 51 are reduced. Furthermore, multiple collimator model outlets 82 with different sizes are marked on one collimator model 8', 8", to achieve a purpose of obtaining multiple sets of irradiation parameters by radiography once, thereby greatly reducing cost of manufacturing the collimator model 8', 8" and cost of radiography of the collimator model 8', 8" and the patient S.

As an effective means for treating cancers, application of neutron capture therapy gradually increases in recent years, in which BNCT is most commonly seen, and neutrons supplied to BNCT may be supplied by a nuclear reactor or accelerator. Preferably, the radiation ray is a neutron beam, the radiation ray generation device 1 is a neutron beam generation device, the radiation ray therapy system is a neutron capture therapy system. More preferably, the neutron capture therapy system is a BNCT system, and further, the BNCT system is an accelerator BNCT system.

The above embodiments are only intended to explain the invention, rather than limiting technical solutions described in the invention, and understanding of the description should be based on those skilled in the art. Although the invention has been described in detail with reference to the above embodiments in the description, it should be understood by those of ordinary skill in the art that those skilled in the art may still make modifications or equivalent substitutions to the invention, and all technical solutions and modifications thereof without departing from the spirit and scope of the invention, shall fall within the scope of claims of the invention.

What is claimed is:

1. A radiation ray therapy system for performing radiation ray therapy of a patient, characterized in that the radiation ray therapy system comprises:
   a radiation ray generation device configured to generate radiation rays for therapy;
   an irradiation chamber configured to place the patient subjected to irradiation of the radiation rays therein;
   a carrying device configured to transport and bear the patient;
   a collimator arranged in the irradiation chamber and comprising a collimator outlet through which the radiation rays emit;
   a collimator model comprising a collimator model outlet with shape and size identical to shape and size of the collimator outlet respectively, a size of the collimator model in a direction perpendicular to the collimator model outlet being smaller than a size of the collimator in a direction perpendicular to the collimator outlet; and
   an irradiation parameter verification device comprising an image acquisition unit configured to acquire image data of the patient and the collimator model.

2. The radiation ray therapy system of claim 1, characterized in that the irradiation parameter verification device further comprises: a storage unit configured to store the image data of the patient and the collimator obtained from the image acquisition unit; a conversion unit configured to convert the image data of the patient and the collimator model in the storage unit into irradiation parameters; a calculation unit configured to calculate dose distribution of the radiation rays in the patient's body at a corresponding position, in combination with the irradiation parameters in the conversion unit; and a comparison unit configured to compare the dose distribution calculated by the calculation unit with a preset dose distribution.

3. The radiation ray therapy system of claim 2, characterized in that the image acquisition unit comprises a computed tomography (CT) scanner.

4. The radiation ray therapy system of claim 1, characterized in that the size of the collimator model in the direction perpendicular to the collimator model outlet is 1 to 10 mm.

5. The radiation ray therapy system of claim 1, characterized in that each collimator model has a plurality of collimator model outlets with different sizes, and shape and size of each of the collimator model outlets correspond to shape and size of a collimator outlet of a corresponding collimator respectively.

6. The radiation ray therapy system of claim 5, characterized in that a plurality of cavities with different sizes are processed inside the collimator model, and each of the cavities with different sizes represents a corresponding collimator model outlet.

7. The radiation ray therapy system of claim 5, characterized in that a plurality of annular grooves with different sizes are formed at intervals on an end face where the collimator model outlet is located, and each of the grooves with different sizes represents a corresponding collimator model outlet.

8. The radiation ray therapy system of claim 1, characterized in that the radiation ray therapy system further comprises an adjustment mechanism configured to adjust and fix a relative position between the patient and the collimator model.

9. The radiation ray therapy system of claim 8, characterized in that the carrying device comprises: a carrying member configured to carry the patient; a driving member configured to drive the carrying member to move; and a connection member connected between the carrying member and the driving member.

10. The radiation ray therapy system of claim 9, characterized in that the radiation ray therapy system is a neutron capture therapy system.

11. An operation method of the irradiation parameter verification device of claim 1, characterized in that the irradiation parameter verification device further comprises: a storage unit configured to store the image data and a preset dose distribution; a conversion unit configured to convert the image data into irradiation parameters; a calculation unit configured to calculate dose distribution of the radiation rays in the patient's body at a corresponding position, in combination with the irradiation parameters; and a comparison unit configured to compare the dose distribution calculated by the calculation unit with the preset dose distribution, comprising the following operations:
S1: the carrying device carrying the patient to move to a working area of the image acquisition unit to acquire the image data of the patient and the collimator model;
S2: storing, by the storage unit, the image data of the patient and the collimator model obtained from the image acquisition unit;
S3: converting, by the conversion unit, the image data of the patient and the collimator model in the storage unit into the irradiation parameters;
S4: calculating, by the calculation unit, dose distribution of the radiation rays in the patient's body when the patient is located at a position corresponding to the irradiation parameters, based on other information, such as beam intensity, tumor size, or the like, in combination with the irradiation parameters;
S5: comparing, by the comparison unit, the dose distribution calculated by the calculation unit with the preset dose distribution; and
S6: adjusting a relative position between the collimator model and the patient, and repeating S1-S5, until a difference between the dose distribution obtained from the calculation unit with the preset dose distribution is within an acceptable range.

12. A radiation ray therapy system for performing radiation ray therapy of a patient, characterized in that the radiation ray therapy system comprises:
a radiation ray generation device configured to generate radiation rays for therapy;
an irradiation chamber configured to place the patient subjected to irradiation of the radiation rays therein;
a carrying device configured to transport and bear the patient;
a collimator arranged in the irradiation chamber and comprising a collimator outlet through which the radiation rays emit; and
a collimator model comprising a collimator model outlet with shape and size identical to shape and size of the collimator outlet respectively, a size of the collimator model in a direction perpendicular to the collimator model outlet being smaller than a size of the collimator in a direction perpendicular to the collimator outlet.

13. The radiation ray therapy system of claim 12, characterized in that the size of the collimator model in the direction perpendicular to the collimator model outlet is 1 to 10 mm.

14. The radiation ray therapy system of claim 12, characterized in that the size of the collimator model in the direction perpendicular to the collimator model outlet is 1 to 10 mm.

15. The radiation ray therapy system of claim 14, characterized in that each collimator model has a plurality of collimator model outlets with different sizes, and shape and size of each of the collimator model outlets correspond to shape and size of a collimator outlet of a corresponding collimator respectively.

16. The radiation ray therapy system of claim 14, characterized in that a plurality of cavities with different sizes are processed inside the collimator model, and each of the cavities with different sizes represents a corresponding collimator model outlet.

17. The radiation ray therapy system of claim 12, characterized in that the radiation ray therapy system further comprises an irradiation parameter verification device configured to verify the patient's position.

18. The radiation ray therapy system of claim 17, characterized in that the irradiation parameter verification device comprises: an image acquisition unit configured to acquire image data of the patient and the collimator model; a storage unit configured to store the image data of the patient and the collimator obtained from the image acquisition unit; a conversion unit configured to convert the image data of the patient and the collimator model in the storage unit into irradiation parameters; a calculation unit configured to calculate dose distribution of the radiation rays in the patient's body at a corresponding position, in combination with the irradiation parameters in the conversion unit; and a comparison unit configured to compare the dose distribution calculated by the calculation unit with a preset dose distribution.

19. A radiation ray therapy system for performing radiation ray therapy of a patient, characterized in that the radiation ray therapy system comprises:
a radiation ray generation device configured to generate radiation rays for therapy;
an irradiation chamber configured to place the patient subjected to irradiation of the radiation rays therein;
a collimator arranged in the irradiation chamber and comprising a collimator outlet through which the radiation rays emit;
a collimator model comprising a collimator model outlet with shape and size identical to shape and size of the collimator outlet respectively, and
an irradiation parameter verification device comprising an image acquisition unit configured to acquire image data of the patient and the collimator model.

20. The radiation ray therapy system of claim 19, characterized in that the irradiation parameter verification device further comprises: a storage unit configured to store the image data of the patient and the collimator obtained from the image acquisition unit; a conversion unit configured to convert the image data of the patient and the collimator model in the storage unit into irradiation parameters; a calculation unit configured to calculate dose distribution of the radiation rays in the patient's body at a corresponding position, in combination with the irradiation parameters in the conversion unit; and a comparison unit configured to compare the dose distribution calculated by the calculation unit with a preset dose distribution.

* * * * *